US009328326B2

(12) United States Patent
Rossmanith et al.

(10) Patent No.: US 9,328,326 B2
(45) Date of Patent: May 3, 2016

(54) METHOD FOR ISOLATING CELLS

(75) Inventors: Peter Rossmanith, Gaaden (AT);
Ingeborg Hein, Vienna (AT); Martin Wagner, Vienna (AT)

(73) Assignee: MERCK PATENT GMBH, Darmstadt (DE)

( * ) Notice: Subject to any disclaimer, the term of this patent is extended or adjusted under 35 U.S.C. 154(b) by 1378 days.

(21) Appl. No.: 12/376,587

(22) PCT Filed: Aug. 10, 2007

(86) PCT No.: PCT/AT2007/000388
§ 371 (c)(1),
(2), (4) Date: Feb. 6, 2009

(87) PCT Pub. No.: WO2008/017097
PCT Pub. Date: Feb. 14, 2008

(65) Prior Publication Data
US 2010/0184210 A1 Jul. 22, 2010

(30) Foreign Application Priority Data
Aug. 10, 2006 (AT) ................................ A 1346/2006

(51) Int. Cl.
| C12Q 1/02 | (2006.01) |
| C12Q 1/00 | (2006.01) |
| C12Q 1/68 | (2006.01) |
| G01N 33/53 | (2006.01) |
| C12Q 1/37 | (2006.01) |
| C12N 1/00 | (2006.01) |
| C12N 1/12 | (2006.01) |
| C12N 1/02 | (2006.01) |
| C12Q 1/24 | (2006.01) |

(52) U.S. Cl.
CPC ... *C12N 1/02* (2013.01); *C12Q 1/24* (2013.01)

(58) Field of Classification Search
USPC ........ 435/2, 6, 174, 242, 252.1, 254.1, 257.1, 435/267, 270, 255.1, 6.1, 4, 7.2, 23, 29, 435/254.7
See application file for complete search history.

(56) References Cited

U.S. PATENT DOCUMENTS

| 3,745,090 | A | * | 7/1973 | Chappelle et al. ................. 435/8 |
| 4,673,344 | A | * | 6/1987 | Chandra et al. ................. 530/344 |
| 5,234,809 | A | * | 8/1993 | Boom et al. ................... 435/91.2 |
| 5,346,999 | A | | 9/1994 | Cathcart et al. |
| 5,420,017 | A | * | 5/1995 | Tuompo et al. ................. 435/29 |
| 5,447,864 | A | * | 9/1995 | Raybuck et al. ............. 435/270 |
| 5,459,253 | A | | 10/1995 | Wolin et al. |
| 5,691,163 | A | * | 11/1997 | Cameron et al. ................. 435/41 |
| 5,827,685 | A | * | 10/1998 | Lindquist ...................... 435/69.1 |
| 6,617,105 | B1 | | 9/2003 | Rudi et al. ................... 435/6.11 |
| 2001/0007153 | A1 | * | 7/2001 | Brown et al. ..................... 800/8 |
| 2002/0072590 | A1 | * | 6/2002 | Van Eyk et al. ............... 530/412 |
| 2002/0127587 | A1 | | 9/2002 | Simms et al. |
| 2002/0177137 | A1 | | 11/2002 | Hodge |
| 2003/0046722 | A1 | * | 3/2003 | Collas et al. ..................... 800/21 |
| 2003/0077841 | A1 | * | 4/2003 | Bouvet et al. ................. 436/518 |
| 2003/0101476 | A1 | * | 5/2003 | Short et al. ..................... 800/278 |
| 2003/0137656 | A1 | * | 7/2003 | Fuse ............................. 356/124 |
| 2003/0153028 | A1 | * | 8/2003 | Refseth et al. ................... 435/34 |
| 2004/0058835 | A1 | * | 3/2004 | Singh et al. ..................... 510/351 |
| 2004/0132082 | A1 | * | 7/2004 | Gautsch et al. ..................... 435/6 |
| 2004/0171077 | A1 | * | 9/2004 | Lubenow et al. .............. 435/7.1 |
| 2004/0248089 | A1 | | 12/2004 | Banada et al. |
| 2005/0009036 | A1 | * | 1/2005 | Montesclaros et al. ........... 435/6 |
| 2005/0224097 | A1 | * | 10/2005 | Medina ........................ 134/25.3 |
| 2005/0244943 | A1 | * | 11/2005 | Ladisch et al. ............. 435/252.3 |
| 2006/0046261 | A1 | * | 3/2006 | Porter et al. ..................... 435/6 |
| 2007/0077562 | A1 | * | 4/2007 | Hossain et al. ................... 435/6 |
| 2008/0131955 | A1 | * | 6/2008 | Stone ............................. 435/270 |
| 2009/0136984 | A1 | * | 5/2009 | Schutz et al. ................... 435/29 |

FOREIGN PATENT DOCUMENTS

| DE | 196 07 202 | 8/1997 |
| WO | WO-02 16947 | 2/2002 |
| WO | WO-03 080865 | 10/2003 |

OTHER PUBLICATIONS

Stevens et al., Bacterial Separation and concentration from complex sample matrices : A review. Critical Reviews in Microbiology 30(1) :7 (2004—cited in search report for PCT/AT07/00388.*
Search report/Written opinion in PCT/AT07/00388.*
Jay et al., Comparison of homogenizing, shaking, and blending on the recovery of microorganisms and endotoxins from fresh and frozen ground beef as assessed by plate counts and the Limulus amoebocyte lysate test. Applied and Environmental Microbiology 38 (5) : 879 (1979).*
Besse et al., Development of a membrane filtration method for enumeration of Listeria monocytogenes from soft cheese. Food Microbiology 18 : 669(2001).*
Record et al, Responses of *E. coli* to osmotic stress: large changes in amounts of cytoplasmic solutes and water, 1998, TIBS, 23, 143-148.*
Klausegger et al, Gram Type-Specific Broad-Range PCR Amplification for Rapid Detection of 62 Pathogenic Bacteria, 1999, Journal of Clinical Microbiology, 37, 464-466.*

(Continued)

*Primary Examiner* — Narayan Bhat
(74) *Attorney, Agent, or Firm* — Millen, White, Zelano, Branigan, P.C.

(57) ABSTRACT

The present invention relates to a method for isolating cells from a complex sample comprising the steps of:
a) providing a complex sample,
b) incubating said sample with:
at least one chaotrope,
a buffer and
at least one detergent,
c) isolating said cells from the resulting mixture by centrifugation or filtration.

31 Claims, 1 Drawing Sheet

(56) References Cited

OTHER PUBLICATIONS

Data sheet Sorbitol structure, Down loaded from the internet [www.sigmaaldrich.com], printed on Apr. 9, 2013, p. 1.*
Data sheet Tween 80, Down loaded from the internet [www.sigmaaldrich.com], printed on Apr. 9, 2013, pp. 1-2.*
Rao et al, Arginine Delays the Onset of Selenite-induced Cataract and Increases in vitro Chaperon-like Activity of Alpha Crystallin, 2005, Invest Ophthalmol Vis Sc., 46, E-Abstract 4700.*
Data sheet Arginine Molecular weight (Sigma), printed on Feb. 9, 2015, pp. 1-2.*
Mayrl et al, Broad Range Evaluation of the Matrix Solubilization (Matrix Lysis) Strategy for Direct Enumeration of Foodborne Pathogens by Nucleic Acids Technologies, 2009, Journal of Food Protection, 72, 1225-1233.*
Mester et al, Use of Ionic Liquid-Based Extraction for Recovery of *Salmonella typhimurium* and *Listeria monocytogenes* from Food Matrices, 2010, Journal of Food Protection, 2010, 73, 680-687.*
Rossmanith et al, Development of matrix lysis for concentration of gram positive bacteria from food and blood, 2007, Journal of Microbiological Methods, 69, 504-511.*
Jian, H. et al., "Glycine betaine supplied exogenously enhance salinity tolerance of pseudomonas putida DLL-1," 2006, vol. 46, No. 1, pp. 154-157.
Reyes Parra, J. E. et al., "Comparison of diverse processing methods simples for the recovery of the epiphytic microflora of fruits," 2006, pp. 55-59.

* cited by examiner

METHOD FOR ISOLATING CELLS

This application is a National Stage entry of PCT/AT2007/000388 filed on Aug. 10, 2007, which claims priority to AU 13462006, filed Aug. 10, 2006.

The isolation of cells from complex samples for their identification or characterisation or simply for further processing is becoming increasingly important, in particular the identification of pathogens in samples like food samples. However, in order to clearly identify and optionally to quantify the cells comprised in a sample methods for their isolation have to be provided.

Real-time PCR has greatly enhanced the application field of PCR as a quantitative tool in molecular biology in general and for the quantification and identification of microorganisms, in particular of pathogens. Real-time PCR allows the reliable detection and quantification down to one single nucleic acid target per PCR reaction requiring highly purified template DNA. Especially when it comes to routine diagnostics and quantitative detection of bacteria in complex environments like food these requirements play a key role as inhibitory effects caused by components of these environments may influence or even inhibit the PCR reaction. Furthermore it is crucial to use a reliable and efficient recovery method to be used for the isolation of the target organisms from complex samples like food. Since samples like food involve generally large sample volumes microbiological methods are normally used for microorganism isolation and enrichment. These methods represent the "golden standard" methods and new alternative techniques have to be evaluated in comparison to them.

Major efforts have been made to establish methods for the separation of microorganisms, e.g. of bacteria, from food which meet the demanding requirements of real time PCR and other molecular methods for downstream analysis of the microorganisms. Also the isolation of DNA directly out of food has been attempted using DNA isolation methods commonly used in molecular biology. Other methods utilize the affinity of biomolecules to surface structures of microorganisms, whereby said biomolecules may be, for instance, antibodies, bacteria binding proteins from phages and antimicrobial peptides (AMPs) optionally in combination with magnetic beads, silanized glass slides or direct colony blot. For instance, for the direct detection of *Listeria monocytogenes* an aqueous two-phase separation system can be used (Lantz et al. Appl Environ Microbiol. (1994) 60:3416-3418). Buoyant density gradient centrifugation is reported as a tool for separation of bacteria from food matrices (Wolffs P. et al. Appl Environ Microbiol. (2005) 71:5759-5764). Other methods are based on physical separation such as simple centrifugation and filtration. Methods applying enzymatic digestion of the food matrix using proteinase K and pronase and/or chemical extraction of the bacteria from food using guanidine thiocyanate/phenol/chloroform, diethylether/chloroform, and sodium citrate/polyethylene glycol have also been described. Current methods for isolating cells, in particular microorganisms, from complex samples are described in, e.g., Stevens K A and Jaykus L A (Crit. Rev Microbiol (2004) 30:7-24).

Most of these methods have drawbacks like insufficient size of processed sample volume, high detection limits, low recovery rates, no quantitative isolation of viable cells, time consuming procedure and high costs. In addition the application of these methods has been restricted in most cases to only one or a limited number of different food matrices. Based on the requirements for direct quantification of bacteria in food which are (i) a large sample volume, (ii) a reproducible recovery rate over a broad range of target concentration, and (iii) removal of inhibitors to aid alternative molecular methods for downstream analysis, new protocols for separation of cells and microorganisms, like the food pathogen *L. monocytogenes*, have to be provided.

WO 2005/010186 relates in particular to a method for determining *Mycobacterium tuberculosis* in a clinical sample. Said method involves the incubation of the sample with a solution comprising guanidinium hydrochloride and a Tris/HCl buffer with a basic pH value. The pellet resulting from a centrifugation step can be used to identify *Mycobacterium tuberculosis*.

WO 01/88183 relates to a method for isolating *Helicobacter pylori* from clinical samples like sputum. In the course of said isolation urea is added to the sample in order to protect urease-positive bacteria like *helicobacter pylori* from high concentrations of acids which are added in the course of the isolation.

US 2006/0046261 relates to buffer solutions comprising detergents and chaotropic substances which can be employed for cell lysis in the course of protein extraction from cells.

It is an object of the present invention to provide means and methods for the quantitative and reproducible isolation of cells from a complex matrix like food and blood.

Therefore the present invention relates to a method for isolating cells from a complex sample comprising the steps of:
a) providing a complex sample,
b) incubating said sample with:
at least one chaotrope,
a buffer and
at least one detergent,
c) isolating said cells from the resulting mixture by centrifugation and/or filtration.

It surprisingly turned out that the incubation of a complex sample with at least one chaotrope in combination with a buffer results in the dissolution of the sample without affecting cells comprising or being surrounded with a cell wall contained in said sample. Therefore the method according to the present invention can suitably be employed for the isolation of such cells.

After the dissolution of the sample the cells initially present in said sample can be isolated by various methods. One isolation method is centrifugation (preferably at 1000 to 8000 g, more preferably at 1500 to 6000 g, even more preferably at 2000 to 5000 g). After the centrifugation step the cells can be found in the pellet and the supernatant can be discarded. If the sample/chaotrope/buffer mixture is filtered the cells are retained on the surface of said filter, when the pore size of the filter is adapted to the size of the cells to be isolated. Of course it is also possible to apply more than one filtration steps with different filters having varying pore sizes. After the filtration step the cells can be washed from the filter surface (see e.g. Stevens K A and Jaykus L-A, Crit. Rev Microbiol (2004) 30:7-24). Filtration of the lysed sample is in particular required when the complex sample comprises material which will hardly or not be lysed with the method of the present invention. Typically these materials comprise starch and/or fibers. However, the preferred method for isolation the cells from the lysis mixture is centrigation.

Of course it is also possible to isolate the cells from the dissolved pellet formed after the centrifugation step by immunological methods involving antibodies, in particular antibodies immobilized on beads, preferably magnetic beads, which are directed to epitopes present on the cells to be isolated. Since the use of antibody beads for isolating cells results in some cases in a reduced recovery rate, such methods may preferably employed mainly for qualitative isolation.

In order to facilitate the dissolution of the sample, said sample can be, for instance, homogenized using a stomacher prior its incubation with the chaotrope and buffer. The dissolution is further supported and/or accelerated when the sample/chaotrope/buffer mixture is agitated during the incubation.

The incubation step may—depending on the sample matrix be repeated once, twice, three times, four times, five times or ten times. Between these incubation steps the cells and the remnant sample matrix may be separated from the supernatant by e.g. centrifugation.

The cells isolated with the method according to the present invention may be used for quantitatively or qualitatively determining the cells in the sample. This can be achieved, for instance, by cell counting, by PCR methods, in particular by real-time PCR, by using lectins or by methods involving antibodies directed to surface structures of said cells (e.g. cell specific ELISA or RIA).

According to the present invention the method may be used preferably to isolate cells surrounded by a cell wall, whereby the term "cells surrounded by a cell wall" refers to all cells known having or comprising a cell wall as a barrier to the environment. Examples for organisms or cells having a cell wall are bacteria, archaea, fungi, plants and algae. In contrast thereto, animals and most other protists have cell membranes without surrounding cell walls.

The term "complex sample" refers to a sample or sample matrix comprising a greater or lesser number of different compounds of mainly organic origin, certain of which are liquid and others of which are solid. A complex sample according to the present invention may comprise peptides, polypeptides, proteins (including also enzymes), carbohydrates (complex and simple carbohydrates), lipids, fatty acids, fat, nucleic acids etc. The sample according to the present invention comprises preferably a low amount of fibers/starch.

As used herein, the term "sample with a low amount of fibers/starch" is used in a broad sense and is intended to include a variety of samples that contain or may contain cells. Preferred samples comprise less than 20% (w/w), more preferably less than 10%, even more preferred less than 5%, especially preferred less than 1%, in particular no (under or around the detection limit), fibers/starch. "Fibers", as used herein, comprise fibers of plant as well as of animal (e.g. collagen fibres) origin.

Exemplary samples include, but are not limited to, food (e.g. milk of cows, ewes, nanny goats, mares, donkeys, camels, yak, water buffalo and reindeer, milk products, meat of beef, goat, lamb, mutton, pork, frog legs, veal, rodents, horse, kangaroo, poultry, including chicken, turkey, duck, goose, pigeon or dove, ostrich, emu, seafood, including finfish such as salmon and tilapia, and shellfish such as mollusks and crustaceans and snails, meat products, plant products seeds, cereals from grasses, including maize, wheat, rice, barley, sorghum, and millet, cereals from non-grasses, including buckwheat, amaranth, and quinoa, legumes, including beans, peanuts, peas, and lentils, nuts, including almonds, walnuts, and pine nuts, oilseeds, including sunflower, rape and sesame, vegetables like root vegetables, including potatoes, cassava and turnips, leaf vegetables, including amaranth, spinach and kale, sea vegetables, including dulse, kombu, and dabberlocks, stem vegetables, including bamboo shoots, nopales, and asparagus, inflorescence vegetables, including globe artichokes, broccoli, and daylilies, and fruit vegetables, including pumpkin, okra and eggplant, fruits, herbs and spices, whole blood, urine, sputum, saliva, amniotic fluid, plasma, serum, pulmonary lavage and tissues, including but not limited to, liver, spleen, kidney, lung, intestine, brain, heart, muscle, pancreas and the like. The skilled artisan will appreciate that lysates, extracts or (homogenized) material obtained from any of the above exemplary samples are also within the scope of the invention.

The term "chaotrope" as used herein, refers to a substance that causes disorder in a protein or nucleic acid by, for example, but not limited to, altering the secondary, tertiary or quaternary structure of a protein or a nucleic acid while leaving the primary structure intact. Exemplary chaotropes include, but are not limited to, guanidine hydrochloride (GuHCl), guanidinium thiocyanate (GuSCN), sodium thiocyanate (KSCN), sodium iodide, sodium perchlorate, urea, and the like. A typical anionic chaotropic series, shown in order of decreasing chaotropic strength, includes: $CCl_3COO^- >> CNS^- > CF_3COO^- > ClO_4^- > I^- > CH_3COO^{2-} > Br^-, Cl^-,$ or $CHO_2^-$. Descriptions of chaotropes and chaotropic salts can be found in, for instance, in K. Hamaguchi et al. (Proc. Natl. Acad. Sci. (1962) 62:1129-1136).

The term "buffer," as used herein, refers to aqueous solutions or compositions that resist changes in pH when acids or bases are added to the solution or composition. This resistance to pH change is due to the buffering properties of such solutions. Thus, solutions or compositions exhibiting buffering activity are referred to as buffers or buffer solutions. Buffers generally do not have an unlimited ability to maintain the pH of a solution or composition. Rather, they are typically able to maintain the pH within certain ranges, for example between pH 7 and pH 9. Typically, buffers are able to maintain the pH within one log above and below their $pK_A$ (see, e.g. C. Mohan, Buffers, A guide for the preparation and use of buffers in biological systems, CALBIOCHEM, 1999). Buffers and buffer solutions are typically made from buffer salts. The buffer added to the dissolution or lysis mixture guarantees that the pH value in the course of the matrix dissolution will be stabilized. A stabilized pH value contributes to reproducible results, efficient lysis and conservation of the isolated cells.

As used herein, the term "detergent" refers to molecules having lipophilic as well as hydrophilic (i.e. amphiphilic) characteristics. A detergent according to the present invention may comprise, for instance, a fatty acid residue and a hydrophilic (e.g. anionic or cationic) part.

According to a preferred embodiment of the present invention the isolated cells are viable cells.

It was surprisingly found that the cells isolated with the method according to the present invention are viable (at least 10%, preferably at least 30%, more preferably at least 50%, even more preferably at least 70%, most preferably at least 90% of the total intact cells isolated) and can be reproduced on suitable culture media.

As used herein, "viable cells" include cells with active metabolism, preferably propagable, especially cells which are able to multiply.

The cells to be isolated with the method according to the present invention are bacterial cells, preferably Gram-positive or Gram-negative bacterial cells, fungal cells, archaeal cells, algae cells or plant cells. Particularly preferred cells are selected from the group consisting of *Listeria* spp., *S. aureus, P. paratuberculosis, Salmonella* spp., *C. jejuni* and *Penicillum roquefortii*.

The method of the present invention allows the isolation of cells having or comprising a cell wall. Due to the presence of a cell wall as the outer barrier the cells can be subjected to substances like chaotropes without affecting their viability.

The present invention specifically allows isolation of microbial cells in general, preferably food and pathogen microbes, especially than of relevance for humans, e.g. potentially present in human food or human pathogen. Therefore the method of the present invention allows to isolate bacterial cells, in particular Gram-positive bacterial cells, fungal cells, archaeal cells, algae cells and plant cells from a highly complex sample (e.g. Food). However, the method of the present invention is also applicable for the isolation of Gram-negative cells.

According to a preferred embodiment of the present invention the sample is a food sample, a body fluid, in particular blood, plasma or serum, water or a tissue sample.

Particularly preferred samples are samples with a complex matrix (i.e. comprising among others proteins, lipids, carbohydrates etc.) and/or a high viscosity.

If the sample, in particular the food sample, comprises collagen and/or starch in an amount of, e.g., over 10%, said sample may be treated with substances capable of degrading at least partially the collagen and starch content prior its incubation with the matrix lysis system of the present invention. Said substances may, for instance, be enzymes like starch degrading enzymes (e.g. cyclodextrin glucanotransferase, alpha-amylase, beta-amylase, glucoamylase, pullulanase and isoamylase).

The food sample is preferably a milk product, preferably milk, in particular raw milk, milk powder, yoghurt, cheese or ice cream, a fish product, preferably raw fish, a meat product, preferably raw meat, meat rinse or sausages, salad rinse, chocolate, egg or egg products, like mayonnaise.

Particularly preferred food samples used in the method according to the present invention are samples which are usually known to comprise potentially pathogenic organisms (e.g. *L. monocytogenes*) and from which cells are—due to a complex matrix—hardly extractable with the methods known in the art. In particular cheese is known as a food with a complex matrix and high viscosity.

According to a preferred embodiment of the present invention the chaotrope is selected from the group consisting of urea, guanidine HCl, guanidine thiocyanate, guanidium thiosulfate, thiourea, sodium thiocyanate (KSCN), sodium iodide, sodium perchlorate and combinations thereof.

It turned out that in particular these chaotropes can be used in the method of the present invention, because they surprisingly do not substantially affect the viability of the cells to be isolated and at the same time allow the dissolution of the sample.

The sample is preferably incubated with a solution comprising 50 mM to 10 M, preferably 200 mM to 9 M, more preferably 1 M to 8 M, of said chaotrope, also depending on the chaotropicity of the specific chaotrope used. Usually, the values herein are drawn to urea; concentrations of other chaotropes may be adjusted by the skilled man in the art by comparing chaotropic properties of a specific chaotrope with urea.

The chaotrope can be employed in a wide concentration range. The best concentration mainly depends on the sample to be dissolved and the chaotrope used. These parameters can be tested easily by the person skilled in the art. Particularly preferred concentrations for urea, e.g., range from 4 to 8 M and for guanidine around 8 M.

According to another preferred embodiment of the present invention the buffer has a pH value greater than 6 and lower than 10, preferably greater than 7 and lower than 9.

The pH value of the buffer may range from 6 to 10, which facilitates the lysis/dissolution of the complex sample and conserves the cells to be isolated. It could be shown that in particular pH values ranging from 7 to 9 result in good lysing results.

The buffer which may be used in the method of the present invention is preferably selected from the group of phosphate buffer, phosphate buffered saline buffer (PBS), 2-amino-2-hydroxymethyl-1,3-propanediol (TRIS) buffer, TRIS buffered saline buffer (TBS) and TRIS/EDTA (TE).

According to a preferred embodiment of the present invention the sample may be additionally incubated with a detergent which is preferably an anionic detergent and/or a zwitterionic detergent.

In order to achieve an even better dissolution of the sample, said sample is additionally incubated with at least one detergent, preferably an anionic detergent and/or zwitterionic detergent and/or non-ionic detergent. The detergent can be added to the sample to reach a final concentration in the mixture of 0.01% to 5%, preferably 0.1% to 3%, more preferably 0.2% to 2%.

The anionic detergent is preferably or sodium dodecyl sulfate (SDS), lithium dodecyl sulfate (LDS) deoxycholate (DOC).

In practise it turned out that the use of sodium dodecyl sulfate (SDS) and lithium dodecyl sulfate (LDS) is less preferred, when Gram-negative bacteria are isolated from a matrix. For cells, like Gram-positive bacteria SDS as well as LDS may be used.

The zwitterionic detergent is preferably 3-[(3-cholamidopropyl)dimethylammonio]-1-propanesulfonate (CHAPS) or 3-[(3-Cholamidopropyl)dimethylammonio]-2-hydroxy-1-propanesulfonate (CHAPSO).

The non-ionic detergent is preferably an ethoxylated aliphatic alcohol, preferably comprising a C13 to C15 aliphatic alcohol. Such ethoxylated aliphatic alcohols are also known as Lutensol. Suitable nonionic detergents are, in particular, acyl, alkyl-, oleyl- and alkylarylethoxylates. These products are obtainable, for example on the market under the name Genapol or Lutensol. This covers, for example, ethoxylated mono-, di- and trialkylphenols (EO (ethyleneoxy group) degree: 3 to 50, alkyl substituent radical: C4 to C12) and also ethoxylated fatty alcohols (EO degree: 3 to 80; alkyl radical: C8 to C36), especially C12-C14-fatty alcohol (3-8) ethoxylates, C13-C15-oxo alcohol (3-30) ethoxylates, C16-C18-fatty alcohol (11-80) ethoxylates, C10-oxo alcohol (3-11) ethoxylates, C13-oxo alcohol (3-20) ethoxylates, polyoxyethylenesorbitan monooleate having 20 ethylene oxide groups, copolymers of ethylene oxide and propylene oxide having a minimum content of 10% by weight of ethylene oxide, the polyethylene oxide (4-20) ethers of oleyl alcohol and also the polyethene oxide (4-20) ethers of nonyl phenol. Use may also be made of mixtures of said nonionic detergents. Non ionic detergents may be used to isolate all kind of cells. However, it surprisingly turned out that the detergents can be employed to isolate in particular Gram-negative cells without affecting said cells.

According to a preferred embodiment of the present invention the incubation is performed at 25° C. to 70° C., preferably 30° C. to 60° C., more preferably 35° C. to 50° C.

In order to dissolve the sample even more efficiently and in a reduced time, it is advantageous to perform the incubation at an elevated temperature. However, care should be taken that elevated temperatures may not affect—if desired—the viability of the cells to be isolated.

After the filtration or centrifugation step the cells are preferably washed with a buffer according to the present invention and/or detergent comprising solutions. However, it is of course possible to add to the wash buffer one or more additional substances. The wash step may be repeated for several times (2, 3, 4, 5 or 10 times) or only once. In the course of the washing step the cells are resuspended in the buffer and then filtered or centrifuged. If in the dissolved sample insoluble particles are present (e.g. calcium phosphate particles of cheese) said particles can be removed either by centrifugation at a lower rotational speed or by letting the particles settle over time (cells will remain in both cases in the supernatant).

The cells may also be washed with detergent comprising solutions. This will allow to further remove fat remnants potentially contained in the cell suspension. Preferred detergents to be used in this method step are those detergents regularly used for fat removal.

A washing step allows in particular the removal of the chaotrope and optionally of the detergent. If these compounds are removed the cells present in the dissolved sample can also be isolated by antibodies bound preferably to a solid support (e.g. beads, in particular magnetic beads). The binding of the cells to antibodies permits to specifically isolate a certain type of cells. This is especially of interest when the sample comprises more than one cell species.

According to a preferred embodiment of the present invention the amount of the cells in the sample is determined.

The amount of the cells in the sample can be determined by any method known in the art, in particular by microbiological methods (e.g. dilution series), cell count, FACS analysis, real-time PCR etc.

According to another preferred embodiment of the present invention the DNA or RNA of the cells is isolated.

Depending on the cells various methods may be employed to extract DNA (e.g. genomic DNA, plasmids) or RNA (e.g. mRNA). All these methods are known in the art and the single protocols mainly depend on the cell to be lysed. The isolation may further require the addition of enzymes like lysozyme.

In order to enhance the lysis of the samples, in particular of samples with a high viscosity (e.g. cheese), said sample is processed by a stomacher or mixer prior incubation.

In order to determine or to monitor the efficiency of the isolation procedure the sample is preferably spiked with a defined amount of cells, which are preferably not identical to the cells present in the sample. The amount of the recovered spiked cells allows to determine the efficiency of the method of the present invention and may also indicate the amount of the cells to be isolated and determined present in the initial sample.

According to a preferred embodiment of the present invention the sample is pre-incubated with a compound exhibiting osmotic stress protective properties to the cells.

In order to increase the resistance of the cells against osmotic stress, the sample comprising (potentially) the cells to be isolated may be incubated with at least one compound which is able to induce osmotic protective responses in said cells. This is especially desired when chaotropes are employed at high molar levels (more than 1 M, preferably more than 2 M).

Compounds exhibiting such characteristics and which are preferably used in the method of the present invention are glycine betaine and/or beta-lysine.

According to a preferred embodiment of the present invention the sample is further incubated with at least one biopolymer degrading enzyme.

Some samples from which the cells are isolated comprise structures of biopolymers which may not or only in an inefficient manner be lysed by the addition of chaotropes and detergents in a buffer. Therefore the sample is preferably incubated further with at least one biopolymer degrading enzyme. Samples which are preferably incubated with biopolymer degrading enzymes are e.g. meat, fish, etc. Ice cream, eggs, blood, milk, milk products etc. do usually not require the addition of biopolymer degrading enzyme. It surprisingly turned out that the use of enzymes alone does not allow the isolation of cells.

As used herein, the term "biopolymer" refers to proteins, polypeptides, nucleic acids, polysaccharides like cellulose, starch and glycogen etc. Therefore a "biopolymer degrading enzyme" is an enzyme which is able to degrade a biopolymer, which may be insoluble in an aqueous buffer (e.g. starch, cellulose), to low molecular substances or even to monomers.

Since the biopolymer degrading enzyme may be active under certain pH and temperature conditions (the use of specific buffers may also play a role) it is advantageous to perform the incubation with said enzymes under optional conditions. These conditions depend on the enzyme used and are known in the art. Also the incubation time depends on extrinsic factors like pH and temperature. Therefore the incubation time may vary from 10 s to 6 h, preferably 30 s to 2 h.

The biopolymer degrading enzyme is preferably selected from the group consisting of proteases, cellulases and amylase, in particular α-amylase. (Savinase 24 GTT (Subtilin), Carenzyme 900 T, Stainzyme GT)

According to another preferred embodiment of the present invention the biopolymer degrading enzyme is incubated with the sample prior to step b) and/or after step c).

The biopolymer degrading enzyme is incubated with sample prior to the addition of the chaotrope and the detergent or after their removal. Since chaotropes and detergents may negatively influence the enzyme activity so that the biopolymers are not efficiently degraded into fragments or monomers, it is advantageous to incubate the sample prior to step b) and/or after step c). Of course if the enzyme is capable to degrade biopolymers under harsh conditions in the presence of chaotropes and detergents it is also possible to incubate the enzyme together with chaotropes and detergents.

Another aspect of the present invention relates to a lysis buffer for the isolation of cells from a complex matrix comprising:
  at least one chaotrope,
  a buffer and
  at least one detergent.

The chaotrope of the lysis buffer is preferably selected from the group consisting of urea, guanidine HCl, guanidine thiocyanate, guanidium thiosulfate, thiourea, sodium thiocyanate (KSCN), sodium iodide, sodium perchlorate and combinations thereof.

The concentration of the chaotrope in the buffer of the present invention is 50 mM to 10 M, preferably 200 mM to 9 M, more preferably 1 M to 8 M.

According to a preferred embodiment of the present invention the buffer has a pH value greater than 6 and lower than 10, preferably greater than 7 and lower than 9.

The buffer of the present invention is selected from the group of phosphate buffer, phosphate buffered saline buffer (PBS), 2-amino-2-hydroxymethyl-1,3-propanediol (TRIS) buffer, TRIS buffered saline buffer (TBS) and TRIS/EDTA (TE).

The detergent is preferably an anionic (e.g. sodium dodecyl sulfate (SDS), lithium dodecyl sulfate (LDS) or deoxycholate (DOC)) and/or zwitterionic detergent (3-[(3-cholamidopropyl)dimethylammonio]-1-propanesulfonate (CHAPS), 3-[(3-Cholamidopropyl)dimethylammonio]-2-hydroxy-1-propanesulfonate (CHAPSO)) and/or a non-ionic detergent (an ethoxylated aliphatic alcohol such as LUTENSOL.

Yet, another aspect of the present invention relates to a kit for the isolation of cells from a complex matrix comprising:
  lysis buffer according to the present invention and
  at least one biopolymer degrading enzyme (see above).

According to a preferred embodiment of the present invention the at least one biopolymer degrading enzyme is selected from the group consisting of proteases, cellulases and amylases, preferably α-amylases.

BRIEF DESCRIPTION OF THE DRAWINGS

The present invention is further illustrated by the following figures and example, however, without being restricted thereto.

EXAMPLES

Example 1

Quantification of *L. monocytogenes* in Milk

Figure 1:
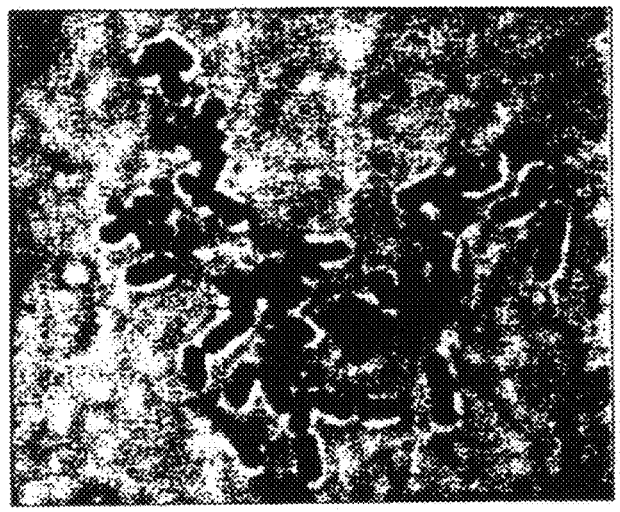
FIG. 1 shows a Gram staining after matrix lysis out of raw milk. The cell wall of the cells isolated (*L. monocytogenes*) were intact.

1. Material and Methods
   1.1. Bacterial Strains and Culture Conditions

*L. monocytogenes* EGDe was used as a DNA quantification standard for real-time PCR and for artificial contamination of food samples. The bacteria were maintained at −80° C. using the MicroBank technology (Pro-Lab Diagnostics, Canada). *Listeria* were grown in tryptone soy broth with 0.6% (w/v) yeast (TSB-Y; Oxoid, UK) at 37° C. over night. For artificial contamination of food and viability staining, one milliliter of the over night culture was transferred to one milliliter of fresh medium and incubated at 37° C. for three hours. Plate count method and tryptone soy agar plates supplemented with 0.6% (w/v) yeast extract (TSA-Y; Oxoid, UK) were used for quantification of the pure cultures of *L. monocytogenes*. The agar plates were incubated at 37° C. for 24 hours. For determination of the survival rate of *L. monocytogenes* treated with different chemical compounds of the matrix lysis buffer system, 100 µl of an overnight culture of *L. monocytogenes* was pelleted at 8,000×g for 5 min, resuspended in the chemical compound of choice, and incubated for 2 h at 45° C. and 300 rpm on an Eppendorf shaker (Eppendorf, Germany). Afterwards the bacterial cells were washed twice in 1×PBS at 5,000×g and resuspended in 120 µl 1×PBS. One-hundred µl of the suspension was plated on PALCAM agar plates (Biokar, Beauvais, France). Incubation was performed 48 h at 37° C.

1.2. Food Samples and Chemical Analysis

All samples used for artificial contamination were tested to be *L. monocytogenes* negative prior to inoculation with the real-time PCR method as described in 1.6. Compositions of raw milk, UHT milk, and hard cheese as used are listed in table 1.

TABLE 1

Composition of milk and hard cheese examined

| Food type | Fat | Protein | Carbohydrates | pH | Ca | Coliforms cfu/ml | Total microbial content cfu/ml |
|---|---|---|---|---|---|---|---|
| Raw milk | 5.4%[a] | 3.7%[a] | 4.8%[a] | 6.5[a] | 0.6-2.0 g/l[c] | $1.6 \times 10^{4a}$ | $4.3 \times 10^{6a}$ |
| UHT milk[b] | 3.5% | 3.3% | 4.7% | 6.7[a] | 1.2 g/l | n.d. | n.d. |
| Hard cheese[c] | 3.1% | 2.8% | 0 | n.d. | 0.02 | n.d. | n.d. |

[a]values measured
[b]specification of manufacturer
[c]Austrian codex alimentarii Determination of the fat content of the raw milk was performed according to ISO 1211:1999 using a gravimetric method. The protein content of the raw milk was determined according to ISO 8968-1:2001 with the Kjeldahl method. Enumeration of coliforms was performed according to IDF standard method 73B:1999 on violet red bile agar (VRB, Merck, Germany) at 30° C. for 24 h. The total count of micro organisms was determined according to IDF standard method 100B:1991 using unselective plate count agar (PCA, Oxoid, UK), at 30° C. for 76 h. For determination of the composition of the remaining pellet resulting from matrix lysis of hard cheese, the pellet was solubilised in solubilisation buffer [30% $HNO_3$ (65%, v/v), 10% HCl (35%, v/v), 20% $H_2O_2$ (30%, v/v) and 30% $H_2O$] in a MLS-Ethos plus (MLS GmbH, Germany) microwave oven for 25 min automatically rising the temperature step less from 20° C. to 200° C. Subsequently the sample was analysed in a Perkin Elmer 3030B atom-absorbing spectrometer (Perkin Elmer, USA) according to the manufacturer's instructions.

1.3. Microscopy

Viability staining was performed by adding 1 µl of component A and 1 µl of component B of the Live/Dead BacLight Bacterial Viability Kit (Molecular Probes, USA) to 1 ml of a $10^{-4}$ dilution of the bacterial cultures in sterile filtrated Ringer's solution (Merck, Darmstadt, Germany). The samples were incubated for 15 min in the dark. Afterwards, 400 µl were filtered onto 0.22-µm-pore size 13 mm black polycarbonate filters (Millipore, USA) using a 5-ml syringe and a Swinnex filter holder (Millipore). 12.7-mm filter discs to test antibiotics (Schleicher & Schuell GmbH, Germany) were placed beneath the polycarbonate filters in the filter holder for support. Viability staining was performed on single samples. Ten fields per filter were analyzed, and two filters were prepared for each sample. To calculate the number of stained cells per ml sample, the following formula was used: N=mean number of cells per field×(effective filtration area/area of the field)×(1/dilution factor)×(1/filtrated volume in ml). Gram staining was performed as known in the art.

1.4. Sample Treatment

For experiments using artificially contaminated samples, 100 µl of a pure culture of *L. monocytogenes* was added to 15 ml raw milk or UHT milk in a 0.50 ml polypropylene tube (Corning, N.Y., USA). Matrix lysis buffer [8 M Urea (Merck, Germany), 1% sodium dodecyl sulphate (SDS, Sigma-Aldrich, Germany) and 1×PBS (155.7 mM NaCl, 2.8 mM KCl, 2.97 mM $Na_2HPO_4$, and 1.06 mM $KH_2PO_4$, pH 7.4)] was added to a final volume of 40 ml. The samples were incubated in a water bath at 45° C. and 200 rpm for 30 min in a horizontal position. Afterwards the samples were centrifuged at 3,220×g for 30 min at room temperature. The supernatant was discarded gently leaving 1 ml in the tubes. The pellet was resuspended in 40 ml washing buffer [1×PBS, 1% Exact industrial detergent (containing anionic detergents and various solvents, pH 7; E. Mayr; Austria)] and incubated in a water bath at 45° C. and 200 rpm for 30 min in a horizontal position. Afterwards the samples were centrifuged at 3,220×g for 30 min at room temperature and the supernatant was gently discarded leaving 500 µl in the tubes. The pellet was re-suspended in 500 µl 1×PBS, transferred into a 1.5 ml plastic tube (Eppendorf, Germany), and washed twice in 1 ml 1×PBS for 5 min at 5,000×g. Hard cheese was added to 12.5 ml matrix lysis buffer in 12.5 g portions and homogenised two times in a Laboratory Blender Stomacher 400 (Seward, UK) for 3 min each. Artificial contamination was performed before homogenisation by adding 100 µl of a pure culture of *L. monocytogenes*. The homogenate was filled in 50 ml polypropylene tubes (Corning, USA), and matrix lysis buffer was added to a volume of 40 ml. The lysis was performed as described for raw milk and UHT milk. The re-suspended pellet was transferred to a 2 ml plastic tube (Eppendorf, Germany) due to pellet size. Two wash steps with 1.5 ml 1×PBS at 5,000×g at room temperature were performed. After re-suspending the pellet in 1.5 ml pre-lysis buffer (20 mM Tris/HCl; 2 mM EDTA; 1% Triton X-100; pH 8), sedimentation of calcium phosphate remnants was allowed for 5 min. The supernatant was transferred to a fresh tube and centrifuged at 8,000×g for 5 min to pellet the bacteria. Subsequently the pellet was subjected to DNA-isolation using the NucleoSpin tissue kit.

Food matrices other than milk or hard cheese (see 2.4. and table 3) were processed in 6 g or 12 g portions, dependent on the liquid content of the food matrix by adding 6 ml or 12 ml of matrix lysis buffer before homogenisation and following the protocol as described for hard cheese with the exception that the re-suspended pellets were transferred to 1.5 ml plastic tubes and that no sedimentation step was necessary.

For experiments analysing the effects of food matrices and detergents contained in the matrix lysis buffer on real-time PCR, food matrices were mixed with equal amounts of ddH2O, stomachered for 3 minutes, diluted in a 10-fold dilution series ($10^{-1}$, $10^{-2}$ and $10^{-3}$) and 5 µl directly subjected to the real time PCR samples. An aliquot was cooked 15 min at 100° C. for comparison prior to subjection of 5 µl to real-time PCR. Detergents were diluted in 2-fold dilution series (0.4 M-0.05 M Urea and 0.8%-0.005% SDS) and 5 µl were subjected to the real-time PCR samples.

DNA isolation of the remaining bacterial pellet after matrix lysis was performed using the NucleoSpin tissue kit (MacheryNagel, Germany and the support protocol for Gram positive bacteria).

1.5. DNA Standard for Real-Time PCR Quantification

One milliliter of a pure culture of *L. monocytogenes* was subjected to DNA isolation using the NucleoSpin tissue kit and the support protocol for Gram positive bacteria. The DNA concentration was measured fluorimetrically using a Hoefer DyNA Quant200 apparatus (Pharmacia Biotech, USA). The copy number of the prfA gene was determined by assuming that based on the molecular weight of the genome of *L. monocytogenes* 1 ng of DNA equals $3.1 \times 10^5$ copies of the entire genome and that the prfA gene is a single-copy gene.

1.6. Real-Time PCR

Real-time PCR was carried out as published previously by targeting a 274 bp fragment of the prfA gene of *L. monocytogenes* using primers LIP1 (5'-GAT ACA GAA ACA TCG GTT GGC-3') SEQ ID NO. 1 and LIP 2 (5'-GTG TAA TCT TGA TGC CAT CAG G-3') SEQ ID NO. 2, and the TaqMan probe LIPprobe2 (5'-FAM-CAG GAT TAA AAG TTG ACC GCA-MGB-3') SEQ ID NO. 3. The TaqMan probe Pluclm-4 (5'-HEX-TTC GAA ATG TCC GTT CGG TTG GC-BHQ1-3') SEQ ID NO. 4 was used for detection of the competitive 100 bp internal amplification control (IAC: 5'-GAT ACA GAA ACA TCG GTT GGC GTA TTC GAA ATG TCC GTT CGG TTG GCG CTA TGA AGA GAT ACG CGG TGG AAC CTG GAA CCT GAT GGC ATC AAG ATT ACA C-3') SEQ ID NO. 5.

The artificial 100 bp target for the IAC was synthesized by VBC Genomics (Austria). Primers and probe Pluclm 4 were purchased at MWG Biotech (Germany). The MGB modified LIPprobe2 was purchased at Applied Biosystems.

Real-time PCR was performed in an Mx3000p real-time PCR thermocycler (Stratagene, USA). The 25 µl volume contained 20 mM Tris-HCl, 50 mM KCl, 3.5 mM MgCl$_2$. 500 nM of each primer, 250 nM of each probe, 200 µM (each) of dATP, dTTP, dGTP and dCTP, 1.5 U of Platinum Taq DNA polymerase (Invitrogen, Austria), 25 copies of the IAC and 5 µM isolated DNA. Amplification following initial denaturation at 94° C. for 2 min was performed in 45 cycles, at each 94° C. for 15 s and 64° C. for 1 minute.

The real-time PCR result was expressed as bacterial cell equivalents (bce). The number of bce/ml was deduced from the volume of the DNA solution after isolation, and the volume of the DNA solution that was finally added to the PCR reaction.

2. Results 2.1. Capability of Different Detergents, Buffer Systems, Solvents, and Additives to Dissolve Food Matrices in Aqueous Solution Combinations of five different detergents (Tween 20, Tween 80, Triton X-100; 1% SDS, CHAPS), four different buffer systems (1×PBS, pH 8; 1×TE, pH 8; 1×TBS, pH 8; 1×Tris, pH 8) and three hydrophilic solvents (8, 6, and 4 M urea; 8 M guanidine; 1 M NaOH) and two lipophilic solvents (CHCl$_3$; n-Hexane) were compared in their ability to dissolve food matrices such as salmon, hard cheese and milk (Table 2).

TABLE 2

Performance of various combinations of buffers, solvents, detergents and additives used in the development of the matrix lysis protocol

|  | 8 M Urea | 6 M Urea | 4 M Urea | 8 M Guanidin | 1 M NaOH | 1 x TBS pH 8[a] |
|---|---|---|---|---|---|---|
| 8 M Urea | n.l.[b] | – | – | – | n.l. | – |
| 6 M Urea | –[c] | n.l. | – | – | – | – |
| 4 M Urea | – | – | n.l. | – | – | – |
| 8 M Guanidine | – | – | – | – | – | – |
| 1 M NaOH | n.l. | – | – | – | n.l. | n.l. |
| 1 x PBS pH 8 | +[d] | n.l. | n.l. | +/ex.[e] | n.l. | – |
| 1 x TE | – | – | – | – | – | – |
| 1 x TBS pH 8[q] | – | – | – | – | – | – |
| 1 x TRIS pH 8[q] | – | – | – | – | – | – |
| 1% SDS | – | – | – | – | n.l. | n.l. |
| Tween 20 (2%) | – | – | – | – | – | – |
| Tween 80 (2%) | – | – | – | – | – | – |
| Triton X-100 (1%) | – | – | – | – | – | – |
| CHAPS | – | – | – | – | – | – |
| CHCl$_3$ | – | – | – | – | – | – |
| n-HEXAN | – | – | – | – | – | – |
| 1 x PBS, 8 M Urea | – | – | – | – | – | – |
| 1 x TBS, 8 M Urea[q] | – | – | – | – | – | – |

TABLE 2-continued

Performance of various combinations of buffers, solvents, detergents and additives used in the development of the matrix lysis protocol

| | | | | | | |
|---|---|---|---|---|---|---|
| 1 x TRIS, 8 M Urea[a] | – | – | – | – | – | – |
| 1 x PBS, 6 M Urea | – | – | – | – | – | – |
| 1 x PBS, 4 M Urea | – | – | – | – | – | – |
| 1 x PBS, 8 M Guanidine | – | – | – | – | – | – |
| 1 x TE, 8 M Urea | – | – | – | – | – | – |
| 1 x PBS, 8 m Urea, 1% SDS[a] | – | – | – | – | – | – |
| 1 x TBS, 8 m Urea, 1% SDS[a] | – | – | – | – | – | – |
| 1 x TRIS, 8 m Urea, 1% SDS[a] | – | – | – | – | – | – |

| | Triton X-100 (1%) | CHAPS | EDTA* | $CHCl_3$ | n-HEXAN | Tween 80 (2%) |
|---|---|---|---|---|---|---|
| 8 M Urea | – | – | – | – | – | – |
| 6 M Urea | – | – | – | – | – | – |
| 4 M Urea | – | – | – | – | – | – |
| 8 M Guanidine | – | – | – | – | – | – |
| 1 M NaOH | – | – | – | – | – | – |
| 1 x PBS pH 8 | n.l. | n.l./ex. | – | n.l./l.p. | n.l. | n.l. |
| 1 x TE | – | – | – | – | – | – |
| 1 x TBS pH 8[a] | – | – | – | – | – | – |
| 1 x TRIS pH 8[a] | – | – | – | – | – | – |
| 1% SDS | n.l. | – | – | n.l./l.p. | n.l. | n.l. |
| Tween 20 (2%) | n.l. | – | – | – | n.l. | n.l. |
| Tween 80 (2%) | n.l. | – | – | – | n.l. | n.l. |
| Triton X-100 (1%) | – | – | – | – | n.l. | n.l. |
| CHAPS | – | n.l./ex. | – | – | ex./n.l. | – |
| $CHCl_3$ | – | – | – | n.l./l.p. | – | – |
| n-HEXAN | n.l. | – | – | – | n.l. | n.l. |
| 1 x PBS, 8 M Urea | n.l. | – | – | – | – | n.l. |
| 1 x TBS, 8 M Urea[a] | n.l. | – | – | – | – | n.l. |
| 1 x TRIS, 8 M Urea[a] | n.l. | – | – | – | – | n.l. |
| 1 x PBS, 6 M Urea | n.l. | – | – | – | – | n.l. |
| 1 x PBS, 4 M Urea | n.l. | – | – | – | – | n.l. |
| 1 x PBS, 8 M Guanidine | n.l. | – | – | – | – | n.l. |
| 1 x TE, 8 M Urea | – | – | – | – | – | – |
| 1 x PBS, 8 M Urea, 1% SDS[a] | – | – | ++ | – | + | – |
| 1 x TBS, 8 M Urea, 1% SDS[a] | – | – | ++ | – | – | – |
| 1 x TRIS, 8 M Urea, 1% SDS[a] | – | – | ++ | – | – | – |

| | 1 x TE[a] | 1 x PBS pH 8 | 1 x TRIS pH 8[a] | 1% SDS | Tween 20 (2%) |
|---|---|---|---|---|---|
| 8 M Urea | – | + | – | – | – |
| 6 M Urea | – | n.l. | – | – | – |
| 4 M Urea | – | n.l. | – | – | – |
| 8 M Guanidine | – | n.l./ex. | – | – | – |
| 1 M NaOH | – | n.l. | – | n.l. | – |
| 1 x PBS pH 8 | – | n.l. | – | n.l. | n.l. |
| 1 x TE | – | – | – | n.l. | – |
| 1 x TBS pH 8[a] | – | – | – | n.l. | – |
| 1 x TRIS pH 8[a] | – | – | – | n.l. | – |
| 1% SDS | n.l. | n.l. | n.l. | n.l. | n.l. |
| Tween 20 (2%) | – | n.l. | – | n.l. | n.l. |
| Tween 80 (2%) | – | n.l. | – | n.l. | n.l. |
| Triton X-100 (1%) | – | n.l. | – | n.l. | n.l. |
| CHAPS | – | n.l./ex. | – | – | – |
| $CHCl_3$ | – | n.l./l.p.[f] | – | n.l./l.p. | – |
| n-HEXAN | – | n.l./l.p. | – | + | n.l. |
| 1 x PBS, 8 M Urea | – | – | – | ++[g] | n.l. |
| 1 x TBS, 8 M Urea[a] | – | – | – | ++ | n.l. |
| 1 x TRIS, 8 M Urea[a] | – | – | – | ++ | n.l. |
| 1 x PBS, 6 M Urea | – | – | – | + | n.l. |
| 1 x PBS, 4 M Urea | – | – | – | + | n.l. |
| 1 x PBS, 8 M Guanidine | – | – | – | ++/ex. | n.l. |
| 1 x TE, 8 M Urea | – | – | – | ++ | – |
| 1 x PBS, 8 M Urea, 1% SDS[a] | – | – | – | – | – |
| 1 x TBS, 8 M Urea, 1% SDS[a] | – | – | – | – | – |
| 1 x TRIS, 8 M Urea, 1% SDS[a] | – | – | – | – | – |

[a]Tested to avoid the formation of calcium phosphate [Ca3(PO4)2] remnants in hard cheese.
[b]n.l. indicates no lysis.
[c]– indicates that this combination was not performed.
[d]+indicates that the resulting pellet hindered subsequent handling (due to pellet size and/or consistency).
[e]ex. indicates that this reagent was considered too expensive and therefore excluded from the protocol.
[f]l.p. indicates a lethal procedure for Listeria.
[g]++, indicates that the resulting pellet permitted good subsequent handling.

Non-ionic detergents like Tween 20, Tween 80, and Triton X-100 showed insufficient lysis when used individually or in combination with different buffers or solvents. The anionic detergent SDS and the zwitterionic detergent CHAPS also led to insufficient lysis of food matrices when used individually, whereas when used in combination with 8 M Urea or 8 M Guanidine good performance was achieved. 1M NaOH used as solvent showed insufficient lysis performance used alone or in combination with 1% SDS. All four buffer systems tested worked well in combination with 1% SDS and 8 M Urea. CHCl₃ and n-Hexane were introduced to dissolve the fat present in the food matrices. These lipophile solvents formed a viscous gel in combination with 8 M urea and 1% SDS thus hindering proper centrifugation. Finally, a combination of 1×PBS, 8 M urea, and 1% SDS was chosen as the matrix lysis buffer. Following the lysis of the food matrices a washing step in 1% industrial detergent Exact in 1×PBS (washing buffer) was introduced to solve fat remnants and to release *L. monocytogenes* cells bound to the 50 ml polypropylene tube.

2.2. Optimization of Centrifugation Steps, pH of Matrix Lysis and Washing Buffer, and Incubation Times and Temperatures Applied The optimal centrifugal force necessary for a maximum recovery of *L. monocytogenes* was tested using 1×PBS. A suboptimal yield of *L. monocytogenes* was obtained if centrifugation was performed with less than 2,500×g for 30 min. Tests with various food matrices which are listed in table 3 showed that more than 3,500×g for 30 min led to problems when re-suspending the pellet containing bacteria and food matrix. Thus a centrifugation step of 30 min at 3,220×g was used to collect the bacteria. With respect to the degradation of the food matrix, lysis of the food matrix with the matrix lysis buffer worked well when performed in a pH range between 7.0 and 9.5 resulting in a reduction of pellet size. A pH of less than 7.0 yielded no sufficient reduction of the pellet size. Thus a pH of 8 was chosen for matrix lysis, to obtain optimal conditions for *L. monocytogenes*. Experiments with temperatures ranging from 25° C. to 56° C. for incubation of the samples with the matrix lysis buffer and the washing buffer using different matrices as listed in table 3 proved 45° C. as the optimal incubation temperature. An increase in pellet size resulted from incubation at temperatures below 45° C. A reduction in yield of *L. monocytogenes* was to expect if higher temperatures were used, as cited in literature. Incubation with the matrix lysis buffer and the washing buffer was optimal for 30 min as longer incubation periods showed no improvements in reduction of the food matrix and an unfinished lysis of the food matrix was observed with incubation periods less than 20 min.

2.3. Application of the Optimized Matrix Lysis Protocol to Various Food Matrices Five groups of foodstuffs were examined: dairy products (raw milk, UHT milk, yoghurt, cottage cheese, mozzarella cheese, Camembert, green-veined cheese, various hard cheeses, and ice cream), cooked and smoked fish and meat (ready-to-eat perch, smoked salmon, and ready-to-eat minced meat), carbohydrate-rich cooked products (ready-to-eat rice and ready-to-eat noodles), ready-to-eat sauces (dill sauce and tomato sauce), and egg (Table 3).

| Matrix | Amount processed | Pellet weigth (wet weight) | | Pellet size (wet volume) | | General comments |
|---|---|---|---|---|---|---|
| | | 1st lysis | 2nd lysis | 1st lysis | 2nd lysis | |
| UHT milk | 12.5 ml | n.d.[a] | n.p.[b] | <2 µl | n.p. | — |
| Raw milk | 12.5 ml | n.d. | n.p. | <2 µl | n.p. | — |
| Yoghurt, 3.6% fat in dry matter | 12.5 g | 0.07 g | 0.07 g | 70 µl | 70 µl | pellet mainly bacteria |
| Cottage cheese, 2.2% fat in dry mat | 12.5 g | 0.04 g | 0.038 g | 40 µl | 40 µl | — |
| Mozzarella cheese and brine | 12.5 g | 0.07 g | 0.06 g | 70 µl | 70 µl | pellet mainly bacteria |
| Camembert | 6.25 g | 2.4 g | 1.4 g | n.d. | n.d. | pellet consists mainly of penicillum roqueforti |
| Green-veined cheese | 6.25 g | 2.0 g | 0.9 g | n.d. | n.d. | pellet consists mainly of penicillum roqueforti |
| Hard cheese | 6.25 g | 0.15 g/0.03 g[c] | n.p. | 150 µl/<10 µl[c] | n.p. | good results with sedimentation for 5-10 min |
| Ice cream (vanilla) | 12.5 g | 0.08 g | 0.08 g | 75 µl | 75 µl | — |
| Ice cream (strawberry) | 12.5 g | 0.34 g | 0.34 g | 350 µl | 350 µl | pellet size due to vegetable remnants |
| Cooked perch | 6.25 g | n.d. | 0.42 g | n.d. | 420 µl | total lysis after 4-5 lysis steps |
| Smoked salmon | 6.25 g | n.d. | 1.6 g | n.d. | n.d. | total lysis after 4-5 lysis steps |
| Cooked minced meat | 6.25 g | n.d. | 3 g | n.d. | n.d. | lysis problematic due to heterogenous composition |
| Cooked noodles | 6.25 g | no lysis | no lysis | n.d. | n.d. | no lysis |
| Cooked rice | 6.25 g | no lysis | no lysis | n.d. | n.d. | no lysis |
| Cooked dill sauce | 12.5 g | 0.28 g | 0.28 g | n.d. | n.d. | good lysis of sauce, no lysis of vegetable portion |
| Cooked tomato sauce | 12.5 g | 5 g | 5.5 g | n.d. | n.d. | no lysis of vegetable portion |
| Egg | 12.5 g | 0.25 g/<0.01 g | 0.25 g/<0.01 g | 300 µl/<2 µl | n.d. | pysical removal of chalaza necessary |
| Blood | 12.5 ml | n.d. | n.p. | <2 µl | n.p. | — |

[a] n.d. indicates that this parameter was not determined.
[b] n.p. indicates that this analysis was not performed.
[c] Weight and volume are given for the pellet of the supernatant, which was removed after sedimentation for 5 min.

In addition, the matrix lysis protocol was applied for blood. Within the group of dairy products the lysis of UHT milk, raw milk, yoghurt, mozzarella, and cottage cheese resulted in a pellet of reasonable size for further processing steps such as DNA isolation. A pellet size of <2 µl was achieved with raw milk and UHT milk. Cottage cheese yielded a pellet size of approximately 40 µl, yoghurt and mozzarella one of 70 µl, whereas the lysis of Camembert and green-veined cheese yielded pellet sizes of each 2.2 ml and 1.9 ml after one lysis step. A second lysis step reduced the pellet size to 1.2 ml and 800 µl, respectively. The lysis of 6 g of various types of hard cheese yielded pellet sizes of approximately 150 µl regardless of the degree of cheese ripening. Microscopical analysis showed that the pellet mainly consisted of round crystalline structures which remained insoluble in water, 1M NaOH, and 1N HCl at both 25° C. and 100° C. The stoichiometric ratio of phosphate and calcium, determined with atom-absorbing spectroscopic analysis, confirmed that the major portion of the remaining pellet consisted of $Ca_3(PO_4)_2$. The introduction of a final sedimentation step for 5 min and subsequent centrifugation of the supernatant decreased the pellet size to approximately 10 µl. Ice cream was reduced to 75 µl during matrix lysis if 12 g were applied except for ice cream containing fruit remnants or nuts which remained insoluble and increased the pelletsize to up to 350 µl. Cooked perch and smoked salmon could be lysed completely with five consecutive lysis steps. Cooked minced meat could not be lysed satisfactorily yielding pellet sizes up to 3 ml even after 5 consecutive lysis steps. The carbohydrate-rich foodstuffs tested remained insoluble when processed with the matrix lysis buffer. Tomato sauce and dill sauce were reduced to the vegetable ingredients which remained insoluble. Egg was totally lysed after two consecutive lysis steps except the chalaza of the egg which was removed after the second lysis step before centrifugation. Blood was totally lysed leading to a pellet size <2 µl after one lysis step.

2.4. Effects of the Matrix Lysis Protocol on Growth and Cellular Appearance of *L. monocytogenes*

The chemical compounds used in the matrix lysis protocol (8 M urea, 1% SDS, 1×PBS, industrial detergent Exact) were tested, alone and in combination, for their impact on the growth and cellular appearance of *L. monocytogenes*. The bacteria were able to grow on TSY agar when treated with 8 M urea or 1×PBS. Complete inhibition of growth was observed for 1% SDS and for the combination 8 M Urea, 1% SDS, and 1×PBS. The industrial detergent Exact also completely inhibited growth of *L. monocytogenes* on TSY agar. Nevertheless, microscopical analysis revealed that all treatments inactivated the cells but left them physically intact.

Figure 2:
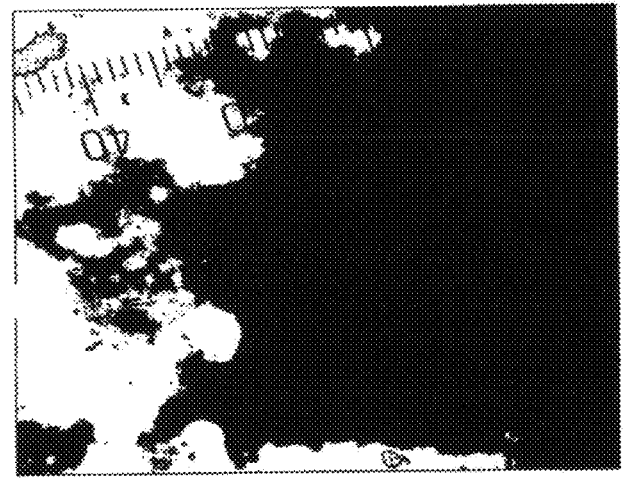
FIG. 2 shows a BacLight staining after matrix lysis of raw milk. With BacLight staining both viable and death cells with damaged cell membranes are fluorescently labelled with fluorophores having different emission wavelengths.

UHT milk containing $2.3 \times 10^5$ (RSD: 38.5%) of cells per milliliter *L. mononcytogenes* and less than 1% inactive cells as determined by microscopy was subjected to the complete matrix lysis protocol was performed. Afterwards, the total cell count was approximately $4.5 \times 10^4$ cells per milliliter and all cells were inactive. It was not possible to determine the cell count in an accurate manner due to a bad signal-to-noise ratio of the weakly stained bacterial cells and the background. The cells remained physically intact after matrix lysis (FIG. 2) which was confirmed by Gram staining (FIG. 1).

2.5. Inhibitory Effects of Food Matrices and Detergents on Real-Time PCR

Real-time PCR reactions containing hard cheese or raw milk diluted from $10^{-1}$ to $10^{-3}$ yielded $C_t$ values of 33.3 (RSD: 0.92%) when containing 15.5 copies of the target gene/PCR and 27.0 (RSD: 1.3%) when containing 1,550 copies of the target gene/PCR. The results were similar if the diluted food samples were boiled before addition to the real-time PCR reaction, yielding Ct values of 33.2 (RSD: 0.26%) and 26.9 (RSD: 0.59%), respectively. For comparison, respective real-time PCR reactions without food matrix yielded Ct values of 32.9 (RSD: 0.57) and 26.7 (RSD: 0.19). These results indicate no inhibitory effects of the food matrices tested on real-time PCR. Analogous experiments with urea and SDS showed inhibitory effects for SDS in a range of 0.8% to 0.005% with no amplification of the targets at the concentrations tested (15.5 and 1,550 copies/PCR). Urea led to total inhibition of the PCR reaction in concentrations of 0.4 M and 0.2 M if 15.5 copies of the target were present and in a concentration of 0.4 M if 1,550 copies of the target were present in the PCR reaction. The $C_t$ values from samples containing 0.1 M and 0.05 M urea were 32.9 (RSD: 2.6%) compared to 32.9 for reactions containing no urea if 15.5 copies were present. The samples containing 1,550 copies of target DNA and urea concentrations of 0.2 M, 0.1 M, and 0.05 M achieved $C_t$ values of 26.1 (RSD: 0.94%) in comparison to 26.3 for samples containing no urea. Thus it was decided to use a column based DNA purification step preceding real-time PCR analysis of the bacterial pellet after matrix lysis.

2.6. Real-Time PCR and Microscopical Analysis of the Recovery of *L. monocytogenes* from Milk After Matrix Lysis Artificially contaminated raw milk and UHT milk containing a decimal dilution series of *L. monocytogenes* in 4 steps starting at $1.07 \times 10^5$ (RSD: 46.9%) cfu per 15 ml of sample was subjected to DNA isolation and real-time PCR after performance of the matrix lysis protocol. The numbers given result from three independently performed experiments with real time PCR samples in duplicates for each kind of milk. The number of bce per sample obtained by real-time PCR from raw milk was $2.0 \times 10^4$ (RSD: 68.3%), $1.9 \times 10^3$ (RSD: 24.4%), $2.2 \times 10^2$ (RSD: 74.8%), and $9.0 \times 10^1$ (RSD: 85.7%). From UHT milk $3.2 \times 10^4$ (RSD: 30.8%), $4.7 \times 10^3$ (RSD: 30.2%), $2.3 \times 10^2$ (RSD: 49.0%), and $6.9 \times 10^1$ (RSD: 51.0%) bce per sample were obtained. Based on these results, which indicate a similar recovery rate at all *L. monocytogenes* concentrations tested, a more detailed investigation was performed by comparing real-time PCR data, total cell counts as determined by microscopy, and cfu before and after performance of the matrix lysis protocol (Table 4).

| | Real-time PCR | | | | |
| --- | --- | --- | --- | --- | --- |
| Recovery related to | Control[a] bce/ml (RSD) | Raw milk bce/ml (RSD) | UHT milk bce/ml (RSD) | Microscopy[b] cells/ml (RSD) | Plate count method[b] cfu/ml (RSD) |
| | $9.3 \times 10^4$ (64.0%) | $2.1 \times 10^4$ (68.4%) | $3.2 \times 10^4$ (30.8%) | $2.2 \times 10^5$ (20.1%) | $1.1 \times 10^5$ (46.9%) |
| Microscopy | 42.0% | 9.3% | 14.0% | 100% | — |
| Plate count method | 86.9% | 19.1% | 29.9% | — | 100% |
| Real-time PCR | 100% | 22.0% | 34.5% | — | — |

[a]Bacterial culture directly processed with NucleoSpin ® tissue kit, without matrix lysis.
[b]Inoculation level of milk before matrix lysis The recovery rate of *L. monocytogenes* specific real-time PCR out of raw milk was 9.3% when compared to the total cell count and 19.1% when compared to the number of cfu. 22.0% yield was achieved when compared to the control sample (real-time PCR analysis of the culture before addition to the milk). For UHT milk the recovery rate of *L. monocytogenes* was 14.0% and 29.9%, respectively, when compared to the total cell count and number of cfu and 34.5% in comparison to the control sample.

3. Concluding Remarks

With the method of the present invention not only fat, carbohydrates and proteins can be removed from a complex sample matrix, like food matrices, in succession or simultaneously but also eucaryotic cells present in the sample can be disintegrated. The remaining cell pellet (preferably bacterial pellet) should be suitable to be further processed with, e.g., alternative DNA-based quantification methods. Raw milk, blue veined cheese, several hard cheeses and salmon were used as model food matrices to establish the matrix lysis protocol and L. monocytogenes was used as model organism because it is of great importance to the food industry. Special care has been given to develop an optimal procedure for the removal of fat from the food matrices. Attempts to separate the fat portion by freezing the samples and to use lipophilic solvents like n-hexan and chloroform turned out to be problematic due to handling problems resulting in incomplete separation or contamination problems and the lipophilic solvents used in the examples, formed viscous gels with the proteins present in the food samples, thus preventing the separation of bacterial cells with centrifugation. The experiments showed that the ability of the matrix lysis protocol containing 1×PBS, 8 M urea and 1% SDS to solve fat was sufficient when performed at elevated temperatures as defined in the present invention (in particular 45° C.). A post-lysis wash step performed in 1% industrial detergent Exact in 1×PBS increased the recovery of L. monocytogenes cells from the food matrix, as fat remnants on the surface of the 50 ml tubes where removed and the adsorption of bacterial cells on the surface of the tubes was prevented.

To develop a useful hydrophilic solvent system a broad range of solvents, detergents, buffer systems and conditions were tested. Based on protocols used in chemical analysis of food NaOH was tested as a solvent in concentrations which have been reported not to affect the integrity of L. monocytogenes cells (<1 M) but the ability of NaOH to solve food matrices was not sufficient in the method of the present invention. Urea and guanidine/HCl were tested since they are widely used in protein biochemistry. Both showed good performance in lysing food matrices when used alone and even better performance when combined with detergents.

Members of three groups of detergents were tested. The non-ionic detergents Tween 20, Tween 80 and Triton X 100 did not significantly contribute to the lysis of the food matrices. Moreover, Triton X-100 cross-reacted with urea as also reported earlier thus deteriorating the performance of the salvation process in 8 M urea. The anionic detergent SDS which is known to bring membrane associated proteins in solution worked well in combination with urea (e.g. 8 M) or guanidine (e.g. 8 M). CHAPS, a zwitterionic detergent, also worked well in combination with urea (e.g. 8 M) or guanidine (e.g. 8 M). A hydrophilic solvent used (e.g. 8 M urea) could easily remove simple sugars whereas starch could not be solved without additional efforts.

Proteins could be solved with good results since the protocol developed is mainly based on concepts originating in protein biochemistry. Thus milk, dairy products, other protein rich food matrices and whole blood were lysed with good performance, which was defined as a resulting pellet size which could easily be processed further using methods to the obtain bacterial DNA from the pellet. The remaining pellet of Camembert and green-veined cheese is composed mainly of a high content of Penicillum roqueforti in both kinds of cheese which could be removed by an additional physical separation step like filtration, sedimentation or simply cutting of the proportions of fungus and bacterial cells. Matrices with higher contents of animal tissues like salmon and perch may require more than one incubation step in the matrix lysis buffer to be dissolved.

The sample volume processed in the present example (6.25 to 12.5 g) is comparatively high. Direct detection or quantification of bacteria in food using alternative DNA-based methods is mainly reported for samples sizes up to 2 g or ml or more. Direct processing of 11 g of plain non fat yoghurt and cheddar cheese 25 ml, 100 ml and 40 ml of raw milk, and 4 g cheese has, for instance, been reported.

Pedersen et al. (Lett. Appl. Microbiol. (1998) 26:47-50), e.g., used the aqueous two-phase system for separation of L. monocytogenes and S. berta from smoked Cumberland sausage processing 4 g. The rational of increasing the sample size is a positive influence on the detection limit. The method presented is also special since it has been tested on a wide range of different kinds of food. In most cases, only a limited number of different food matrices have been tested.

The modification of the matrix lysis protocol as a washing protocol seems possible in all cases where the bacteria contaminate the surface of insoluble food matrices, such as salad, salmon or hard cheese, where L. monocytogenes is mostly introduced during processing. All four buffer Systems which were introduced to obtain constant conditions at a pH of approximately 8 in order to preserve the bacteria during the matrix lysis protocol worked well in combination with the detergents and solvents mentioned above. In addition, the physical conditions for the matrix lysis protocol like temperature and centrifugation forces were adjusted for optimal lysis of the food matrices within the reported range of survival of L. monocytogenes. Gram staining of the remaining bacterial pellet after matrix lysis showed that the cell walls remained intact. This was confirmed further by fluorescent staining of the chromosomal DNA which showed that the DNA remained within the bacterial cells. However the bacteria had been compromised during the lysis process of the food matrix. As the cells showed a red and sometimes an orange colour indicating cell inactivation, whereas living cells should be stained in green color. This was also confirmed by plating of the cells on TSA-Y agar after the lysis protocol. After resuscitation in TSB-Y medium at 37° C. for 2 h the cells resuscitated.

As proof of principle the matrix lysis protocol was tested in combination with real-time PCR to show the ability for direct quantification of L. monocytogenes in raw milk and UHT milk. The NucleoSpin tissue kit for DNA Isolation was used for processing of the bacterial pellet after matrix lysis because an inhibitory effect of urea and SDS on real-time PCR was expected, as preliminary experiments have shown. Efforts to isolate the DNA with a shorter previously used protocol based on boiling of the sample at the presence of Tween 20 yielded no amplification of target DNA with the following real-time PCR. A good reproducibility of the recovery rate of the matrix lysis protocol could be shown as the decimal dilution of the artificial contaminated samples was reflected in the real-time results. The varying recovery rates obtained in relation to the plate count method (CFU) and to the total cell count using the microscope derive from the growing conditions of the bacteria, which were harvested at late log phase to get a maximum of living cells. The cells were actively growing and many of those which underwent cell division were not physically separated from each other yet.

In summary, the matrix lysis protocol presented enables the reduction of 6 to 12 g volumes of various food matrices to small pellets which can be easily used for further processing with DNA-based methods, as has been shown with artificially contaminated milk in combination with real-time PCR analysis. The method is a promising tool towards faster and eventually on-line hygiene monitoring in food production thus adding existing HACCP concepts. Further research should focus on broadening the range of foodstuffs which can be processed using this method, exploring the combination of the protocol with downstream real-time PCR analysis to more details, and application of the method to other food borne bacterial pathogens.

Example 2

In the present example the application of the protocol of the present invention on Gram negative bacteria is shown, whereby it turned out that with the use of proteases and a sucrose buffer the matrix lysis protocol, to incubate microorganisms from chicken, meat and fish, could further be improved. The present protocol was used for dairy products, milk, fish and meat, ice cream, egg and blood. Lysis resulted in pellets of reasonable size for further processing. Using *L. monocytogenes, S. aureus, B. cereus E. coli* and *S. thyphimurium* as model organisms, microscopic analysis of the remaining bacterial pellets revealed that the recovered bacteria remained physically intact. The application of the matrix lysis protocol to salmon, chicken, ice cream, mozzarella, hard cheese and blood using real-time PCR, was shown both with *L. monocytogenes* and *S. thyphimurium* within their artificially contaminated native foodstuffs.

2. Material and Methods 2.2. Bacterial Strains and Culture Conditions

*L. monocytogenes* EGDe, was used as model organism for Gram positive bacteria and as a DNA quantification standard for real-time PCR and for artificial contamination of food samples. *S. aureus* (NCTC 1803) and *B. cereus* (NCTC 7464) were used to analyse the effects of the matrix lysis protocol on the growth and cellular appearance on gram positive bacteria other than *L. monocytogenes. S. thyphimurium* subsp. *thyphimurium*, strain (NCTC 12023) and *E. coli* (ATCC 25922) were used as model organisms for Gram negative bacteria. The bacteria were maintained at −80° C. using the MicroBank™ technology (Pro-Lab Diagnostics, Canada). All bacterial strains were grown overnight in tryptone soy broth with 0.6% (w/v) yeast (TSB-Y; Oxoid, UK) at 37° C. For artificial contamination of food, one milliliter of the overnight culture was transferred to one milliliter of fresh medium and incubated at 37° C. for three hours, and 100 μl of appropriate dilutions in 1×PBS were added to the samples. The plate count method and tryptone soy agar plates supplemented with 0.6% (w/v) yeast extract (TSA-Y; Oxoid, UK) were used for quantification of all bacterial strains used. The agar plates were incubated at 37° C. for 24 hours.

For assessment of the survival rate of the bacteria treated with different chemical compounds of the matrix lysis buffer system, 100 μl of an overnight culture was pelleted at 8,000×g for 5 min, re-suspended in 1 ml of the chemical compound of choice, and incubated for 2 h at 45° C. and 300 rpm on an Eppendorf shaker (Eppendorf, Germany). The bacterial cells were then washed twice in 1×PBS at 5,000×g and re-suspended in 120 μl 1×PBS. One-hundred it of the suspension was plated onto TSB-Y agar plates (Oxoid). Incubation was performed for 48 h at 37° C. Additionally the Live/Dead® BacLight™ Bacterial Viability Kit (Molecular Probes, USA) was used to examine the condition of the bacteria after the chemical treatments.

2.2. Food Samples

All food samples except raw milk and blood were purchased at supermarkets. Raw milk was taken from a dairy farm. All samples used for artificial contamination were tested to be *L. monocytogenes* and *S. thyphimurium* negative using the protocols as described below.

2.3. Microscopic Investigation

Viability staining was performed using the Live/Dead® BacLight™ Bacterial Viability Kit (Molecular Probes) as prescribed by the manufacturer. Ten fields per filter were analysed, and two filters were prepared for each sample.

2.4. Further Development of the Matrix Lysis Protocol and Sample Treatment

Combinations of five different detergents (Tween 20®, Tween 80®, Triton X-100®; SDS, and Lutensol AO-7), three enzymes (Protease, alpha-amylase and cellulase) and a sucrose buffer (0.25 M sucrose, 1 mM EDTA and 0.05 M Tris, pH 7.6) were compared with respect of their ability to dissolve food matrices (salmon, chicken meat, diary products, ice cream, blood, starch rich foodstuffs, egg and milk) and their effect on the cellular appearance of the bacterial cells. All chemicals used (with the exception of SDS, Sigma-Aldrich, Germany; Lutensol AO-7, BASF, Netherland and Savinase, Novozymes, Denmark) were purchased at Merck (Germany). The matrix lysis protocol is described below.

Matrix lysis was generally performed as described in example 1. Processing meat, fish, chicken and blood or when Gram positive bacteria were targeted, buffer system I (8 M urea, 1% SDS, and 1×PBS) was used. Buffer system II (8 M urea, 1% Lutensol AO-7 and 1×PBS) was used if Gram negative bacteria were targeted and for all other foodstuffs used (Milk, diary products, ice cream, and egg).

For experiments using artificially contaminated samples, 100 μl of a pure bacterial culture was added to 12.5 ml of liquid foodstuff or 6.25 g of solid foodstuff in a 50-ml polypropylene tube (Corning, USA).

Meat and fish samples were mixed with 25 ml of sucrose buffer and homogenised in the laboratory blender Stomacher 400 (Seward, UK) for 30 min. The homogenate was transferred to 50-ml polypropylene tubes (Corning, USA), and protease buffer (0.1% Savinase 24 GTT subtilin and 1×PBS) was added to a volume of 40 ml and incubated in a water bath (45° C. if Gram positive bacteria were targeted and 37° C. or 42° C. for *E. coli* and *S. thyphimurium* respectively) and constant shaking at 200 rpm for 30 min in horizontal position. Afterwards the samples were centrifuged at 3,220×g for 30 min at room temperature. The supernatant was discarded gently, leaving 1 ml in the tubes. The pellet was resuspended in matrix lysis buffer 1 up to a final volume of 45 ml. The samples were incubated in a water bath (45° C. if Gram positive bacteria were targeted and 37° C. and 42° C. for *E. coli* and *S. thyphimurium* respectively) and constant shaking at 200 rpm for 30 min in horizontal position. The samples were then centrifuged at 3,220×g for 30 min at room temperature. The pellet was re-suspended in 40 ml washing buffer (1% Lutensol AO-7 and 1×PBS) and incubated in a water bath (45° C. if Gram positive bacteria were targeted and 37° C. and 42° C. for *E. coli* and *S. thyphimurium* respectively) and constant shaking at 200 rpm for 30 min in horizontal position. Afterwards the samples were centrifuged at 3,220×g for 30 min at room temperature and the supernatant was gently discarded. The pellet was resuspended in 500 μl 1×PBS, transferred to a 1.5-ml plastic tube (Eppendorf, Germany), and washed twice in 1 ml 1×PBS with additional centrifugation for 5 min at 5,000×g.

DNA isolation of the remaining bacterial pellet after matrix lysis was performed using the NucleoSpin® tissue kit (MacheryNagel, Germany) and the support protocol for Gram positive bacteria if necessary.

2.5. DNA Standard for Real-Time PCR Quantification

One milliliter of a pure over night culture of *L. monocytogenes* strain EGDe (½a) or *S. thyphimurium* subsp. *thyphimurium*, strain NCTC 12023 was subjected to DNA isolation using the NucleoSpin© tissue kit and the support protocol for gram positive bacteria if necessary. The DNA concentration was measured fluorimetrically using a Hoefer DyNA Quant200 apparatus (Pharmacia Biotech, USA). The copy number of the prfA gene was determined by assuming that when Gram negative bacteria were targeted. Lutensol AO-7 provided good lysis of the food matrix without decreasing the recovery of Gram negative bacteria as SDS did (Table 1).

TABLE 1

Viability and cellular appearance of Gram positive and Gram neg.ative bacteria exposed to different detergents, enzymes and temperatures

| | | E. coli | | S. thyphimurium | | L. monocytogenes | | S. aureus | | B. cereus | |
|---|---|---|---|---|---|---|---|---|---|---|---|
| | C.° | BacLight ™ | Plate growth | BacLight ™ | Plate growth | BacLight ™ | Plate growth | BacLight ™ | Plate growth | BacLight ™ | Plate growth |
| 8 M Urea | 37 | red[a] | neg. | c.r.[b]/red | neg. | green[c] | pos.. | green | pos.. | green | pos.. |
| Lutensol AO-7 (1%) | 37 | green | pos. | — | — | — | — | — | — | — | — |
| Sucrose Buffer | 37 | green | pos. | — | — | — | — | — | — | — | — |
| Protease (Savinase) (0.1%) | 37 | green | pos. | — | — | — | — | — | — | — | — |
| Buffer SystemI | 37 | red | neg. | c.r./red | — | — | — | — | — | — | — |
| Buffer SystemII | 37 | red | neg. | — | — | — | — | — | — | — | — |
| Washing Buffer I | 37 | — | — | — | — | — | — | — | — | — | — |
| Washing Buffer II | 37 | green | pos. | — | — | — | — | — | — | — | — |
| 1xPBS (Control) | 37 | green | pos. | green | — | — | — | — | — | — | — |
| 8 M Urea | 42 | c.r./red | neg. | c.r./red | neg. | green | pos.. | green | pos.. | green | pos.. |
| Lutensol AO-7 (1%) | 42 | — | — | green | pos. | — | — | — | — | — | — |
| Sucrose Buffer | 42 | — | — | green | pos. | — | — | — | — | — | — |
| Protease (Savinase) (0.1%) | 42 | — | — | green | pos. | — | — | — | — | — | — |
| Buffer SystemI | 42 | neg. | — | c.r./red | neg. | — | — | — | — | — | — |
| Buffer SystemII | 42 | c.r./red | — | red | neg. | — | — | — | — | — | — |
| Washing Buffer I | 42 | — | — | — | — | — | — | — | — | — | — |
| Washing Buffer II | 42 | — | — | green | pos. | — | — | — | — | — | — |
| 1xPBS (Control) | 42 | green | — | — | pos. | — | — | — | — | — | — |
| 8 M Urea | 45 | c.r./red | — | c.r./red | neg. | green | pos.. | green | pos.. | green | pos.. |
| Lutensol AO-7 (1%) | 45 | — | — | — | — | — | pos. | — | pos. | — | pos. |
| Sucrose Buffer | 45 | — | — | — | — | green | pos. | green | pos. | green | pos. |
| Protease (Savinase) | 45 | — | — | — | — | green | pos. | green | pos. | green | pos. |
| Buffer SystemI | 45 | neg. | — | c.r./red | — | — | neg. | — | neg. | — | neg. |
| Buffer SystemII | 45 | c.r./red | — | — | — | red | neg. | red | neg. | red | neg. |
| Washing Buffer I | 45 | — | — | — | — | green | pos. | green | pos. | green | pos. |
| Washing Buffer II | 45 | — | — | — | — | green | pos. | green | pos. | green | pos. |
| 1xPBS (Control) | 45 | green | — | — | — | green | pos. | green | pos. | green | pos. |

[a]Red colour indicates dead cells
[b]Reduced cell count
[c]Green colour indicates living cells based on the molecular weight of the genome of *L. monocytogenes*, 1 ng of DNA equals $3.1 \times 10^5$ copies of the entire genome, and that the prfA gene is a single-copy gene (Nelson et al., 2004 Nucleic Acid Res 32: 2386-2395). The copy numbers of the *Salmonella* target were similarly determined by assumption of $2 \times 10^5$ copies of the entire *S. thyphimurium* genome per 1 ng of DNA (McClelland et al., 2001 Nature 413.6858 (2001): 852-56).

2.6. Real-Time PCR

Real-time PCR was carried out as published previously by targeting a 274 bp fragment of the prfA gene of *L. monocytogenes* (D'Agostino et al., 2004 J Food Prot. 67: 1646-1655). *S. thyphimurium* was expressed as bacterial cell equivalents (BCE). All real-time PCR samples were performed in duplicate. s detected using the SureFood® Kit (R-Biofarm, Germany) according to the instruction manual. The real-time PCR result 3. Results 3.1. Ability of Different Detergents, Enzymes, and Additives to Dissolve Food Matrices in Aqueous Solution A more specific composition for the lysis buffers as primarily used for matrix lysis (see example 1)—1xPBS, 8 M urea, and 1% SDS (Lysis buffer I)—was chosen after testing a large number of chemicals to meet the requirements of Gram negative bacteria (Table 1). The lysis buffer II containing 8 M urea, 1% Lutensol AO-7 and 1xPBS was used to solve the matrices A first incubation step in sucrose buffer combined with an upstream incubation in 0.1% protease and subsequent use of lysis buffer I (Gram positive bacteria) or buffer II (Gram negative bacteria) yielded to a pellet size after matrix lysis when processing meat, fish and chicken, which was useful for downstream DNA isolation and real-time PCR. 6.25 g of meat, chicken or smoked salmon yielded in a pellet of a size of approximately 3 ml if processed in sucrose buffer with subsequent incubation in 0.1% protease buffer without the use of buffer I or buffer II during matrix lysis (Table 1).

Following lysis of the food matrices, a washing step in 1% Lutensol AO-7 in 1xPBS was introduced to replace 1% industrial detergent Exact® in 1xPBS as originally used as washing buffer.

3.2. Optimisation of the Temperatures Used for Matrix Lysis Targeting Gram Negative Bacteria Experiments with temperatures ranging from 37° C. to 45° C. for incubation of *E. coli* and *S. thyphimurium* in lysis buffer II showed 37° C. and 42° C. to be the optimal incubation temperature for *E. coli* and *S. thyphimurium* respectively, in terms of viability and cellular appearance of the bacterial cells (Table 1—Viability and cellular appearance of Gram positive and Gram negative bacteria exposed to different detergents, enzymes and temperatures).

3.3. Application of the Optimised Matrix Lysis Protocol to Various Food Matrices With respect to the degradation of the food matrix, lysis of the food matrix with the matrix lysis buffer II worked well when performed with diary products, resulting in a reduction of the pellet size. Within the group of dairy products, the lysis of UHT milk, raw milk, yoghurt, mozzarella, and cottage cheese resulted in a pellet of reasonable size for further processing steps. Lysis of 6.25 g of various types of hard cheeses yielded pellet sizes of approximately 150 µl, regardless of the degree of cheese ripening. As stated above the main part of the pellet consisted of round crystalline structures [$Ca_3(PO_4)_2$] (Example 1). The introduction of a final sedimentation step for 2 min and subsequent centrifugation of the supernatant decreased the pellet size to approximately 10 µl. Ice cream was reduced to 50 µl during matrix lysis if 6.25 g was applied, except when the ice cream contained bits of herbal origin. Smoked salmon, chicken and meat were lysed to approximately 50 µl when homogenised in 0.25 M sucrose buffer for 30 min and subsequently incubated with 0.1% protease buffer prior to the matrix lysis protocol using lysis buffer I (Table 1).

of Gram positive and Gram negative bacteria exposed to different detergents, enzymes and temperatures). The bacteria were able to grow on TSB-Y plates when treated with 0.1% protease, 0.1% alpha amylase and 0.1% cellulase, sucrose buffer or 1% Lutensol AO-7. In combination with 8 M urea bacterial growth was totally inhibited. Microscopic analysis showed that all treatments in combination with the buffer II system (1% Lutensol AO-7 instead of 1% SDS) left the cells physically intact.

3.5. Real-Time PCR of *L. monocytogenes* from Various Foodstuffs After Matrix Lysis Artificial contaminated chicken, smoked salmon, ice cream, Gouda cheese, Mozzarella cheese and blood containing a decimal dilution series of *L. monocytogenes* was subjected to DNA isolation and real-time PCR after application of the matrix lysis protocol. A detailed investigation was performed by comparing real-time PCR data, total cell counts as determined by microscopy and CFU before and after the application of the matrix lysis protocol (Table 2). For detailed information see table 3

TABLE 2

Application of the optimized matrix lysis protocol to various food matrices and blood

| Matrix | Buffer | Sucrose buffer[a] | Protease | Amount processed | Pellet size (wet volume) 1st lysis | Wash | General comments |
|---|---|---|---|---|---|---|---|
| Raw milk | II[b] | no | no | 12.5 g | 30 µl | 30 µl | — |
| UHT milk | II | no | no | 12.5 g | 15 µl | 15 µl | — |
| Yoghurt, 3.6% fat in dry matter | II | no | no | 12.5 g | 70 µl | 70 µl | pellet mainly bacteria |
| Cottage cheese, 2.2% fat in dry matter | II | no | no | 6.25 g | 40 µl | 40 µl | — |
| Mozzarella cheese and brine | II | no | no | 6.25 g | 70 µl | 70 µl | pellet mainly bacteria |
| Hard cheese (Gouda) | II | no | no | 6.25 g | 150 µl/<10 µl[c] | <10 µl | good results with sedimentation for 2 min |
| Hard cheese (Emmentaler) | II | no | no | 6.25 g | 150 µl/<10 µl[c] | <10 µl | good results with sedimentation for 2 min |
| Ice cream (Vanilla) | II | no | no | 6.25 g | 50 µl | 50 µl | — |
| Ice cream (Twinnie) | II | no | no | 6.25 g | 50 µl | 50 µl | — |
| Beef | I[d] | yes | yes | 6.25 g | 40-100 µl | 40-100 µl | — |
| Chicken | I | yes | yes | 6.25 g | 40-100 µl | 40-100 µl | — |
| Smoked salmon | I | yes | yes | 6.25 g | 40-100 µl | 40-100 µl | — |
| Beef | no | yes | yes | 6.25 g | 3 ml | 3 ml | — |
| Chicken | no | yes | yes | 6.25 g | 3 ml | 3 ml | — |
| Smoked salmon | no | yes | yes | 6.25 g | 3 ml | 3 ml | — |
| Egg | I | no | no | 12.5 g | <2 µl | <2 µl | physical removal of chalaza necessary |
| Blood | I | no | no | 12.5 g | <2 µl | <2 µl | — |

[a] 0.25 M sucrose, 1 mM EDTA and 0.05 M Tris, pH 7.6
[b] 1 x PBS, 1% Lutensol AO-7, 8 M Urea
[c] Weight and volume are given for the pellet the supernatant of which was removed after sedimentation for 2 min.
[d] 1 x PBS, 1% SDS, 8 M Urea 3.4. Effects of Enzymes, Detergents and Additives on the Growth and Cellular Appearance of Gram Positive and Gram Negative Bacteria The compounds used in the matrix lysis protocol of this example (Lutensol AO-7, 0.1% protease, 0.1% alpha amylase, 0.1% cellulase and the 0.25 M sucrose buffer) were further tested alone or in combination with 8 M urea and 1xPBS, for their impact on the growth and cellular appearance of *L. monocytogenes*, *S. aureus*, *B. cereus*, *S. thyphimurium* and *E. coli* (Table 1—Viability and cellular appearance 3.6. Real-Time PCR of *S. thyphimurium* from Ice Cream, Egg and Chicken After Matrix Lysis Artificial contaminated chicken, ice cream, and egg containing a decimal dilution series of *S. thyphimurium* was subjected to DNA isolation and real-time PCR after application of the matrix lysis protocol. A detailed investigation was performed by comparing real-time PCR data, total cell counts as determined by microscopy and CFU before and after the application of the matrix lysis protocol (Table 2). For detailed information see table 3.

TABLE 3

Determination of the recovery rate of *L. monocytogenes* and *S. thyphimurium* out of various foodstuffs after matrix lysis as determined by real-time PCR

| Recovery related to | Real-time PCR Control[a] bce/ml (RSD) | Real-time PCR Foodstuff avg.[b] bce/ml (RSD) | Microscopy[c] cells/ml (RSD) | Plate count method[c] cfu/ml (RSD) |
|---|---|---|---|---|
|  | $8.9 \times 10^4$ (64.0%) | $3.1 \times 10^4$ (68.4%) | $1.8 \times 10^5$ (20.1%) | $1.2 \times 10^5$ (46.9%) |
| Microscopy | 49.4% | 17.2% | 100% | — |
| Plate count method | 74.6% | 25.8% | — | 100% |
| Real-time PCR | 100% | 34.8% | — | — |

[a]Bacterial culture directly processed with NucleoSpin ® tissue kit, without matrix lysis
[b]Salmon, chicken, icecream, gouda cheese, mozzarella cheese, egg and blood.
[c]Inoculation level of foodstuff before matrix lysis

The invention claimed is:

1. A method for isolating viable cells with cell walls from a complex sample comprising:
   a) providing a complex sample,
   b) incubating said complex sample at 25° C. to 70° C. for at least 20 minutes with a lysis solution comprising:
      at least one chaotrope in a concentration between 50 mM to 10M, that is urea, guanidine HCl, guanidine thiocyanate, guanidium thiosulfate, thiourea, sodium thiocyanate potassium thiocyanate, sodium iodide, sodium perchlorate or a combinations thereof
      a buffer having a pH of 6 to 10 and
      0.01% to 5% of at least one anionic, non-ionic and/or zwitterionic detergent until dissolution of said complex sample to form a mixture,
   c) subjecting the resultant mixture consisting of said complex sample and said lysis solution from incubation and dissolution step b) to a centrifugation or a filtration and isolating viable cells with cell walls from the resultant mixture whereby said viable cells with cell walls are retained on a filter after the filtration or retained in a pellet after the centrifugation.

2. A method according to claim 1, wherein the cells with cell walls are bacterial cells, fungal cells, archaeal cells, algae cells or plant cells.

3. A method according to claim 2, wherein the cells with cell walls are Gram-positive bacterial cells or Gram-negative bacterial cells.

4. A method according to claim 1, wherein said sample is a food sample, blood, or a tissue sample.

5. A method according to claim 4, wherein the food sample is a milk product, a fish product, a raw fish or a meat product.

6. A method according to claim 5, wherein the milk product is raw milk, milk powder, yoghurt, cheese or ice cream.

7. A method according to claim 4, wherein said food sample is raw meat, meat rinse, sausage, chocolate, egg, an egg product or mayonnaise.

8. A method according to claim 1, wherein the chaotrope is urea, guanidine HCl, guanidine thiocyanate, guanidium thiosulfate, or a combinations thereof.

9. A method according to claim 1, wherein the sample is incubated with a solution comprising 1 M to 8 M of said chaotrope.

10. A method according to claim 9, wherein the sample is incubated with a solution comprising 4M to 8 M, of said chaotrope.

11. A method according to claim 1, wherein the buffer is a phosphate buffer, phosphate buffered saline buffer (PBS), 2-amino-2-hydroxymethyl-1,3-propanediol (TRIS) buffer, TRIS buffered saline buffer (TBS) or TRIS/EDTA (TE).

12. A method according to claim 1, wherein the detergent is an anionic detergent.

13. A method according to claim 12, wherein that the anionic detergent is sodium dodecyl sulfate (SDS), lithium dodecyl sulfate (LDS) or deoxycholate (DOC).

14. A method according to claim 1, wherein the zwitterionic detergent is 3[(3-cholamidopropyl)dimethylammonio]-1-propanesulfonate (CHAPS) or 3-[(3-Cholamidopropyl)dimethylammonio]-2-hydroxy-1-propanesulfonate (CHAPSO).

15. A method according to claim 1, wherein that the non-ionic detergent is an ethoxylated aliphatic alcohol.

16. A method according to claim 15, wherein that the non-ionic detergent comprises a $C_{13}$ to $C_{15}$ aliphatic alcohol.

17. A method according to claim 15, wherein said ethoxylated aliphatic alcohol is a $C_{13}$ to $C_{15}$ aliphatic alcohol.

18. A method according to claim 1, wherein the cells with cell walls are washed after the isolation step with buffer and/or detergent comprising solutions.

19. A method according to claim 1, wherein the amount of the cells with cell walls in the sample is determined.

20. A method according to claim 1, wherein the DNA or RNA of the cells is isolated.

21. A method according to claim 1, wherein the sample is processed by a stomacher or mixer prior to incubation.

22. A method according to claim 1, wherein the sample is spiked with a defined amount of cells.

23. A method according to claim 1, wherein the sample is pre-incubated with a compound exhibiting osmotic stress-protective properties to the cells.

24. A method according to claim 23, wherein said compound is glycine betaine or beta-lysine.

25. A method according to claim 1, wherein the sample is further incubated with at least one biopolymer degrading enzyme.

26. A method according to claim 25, wherein the biopolymer degrading enzyme is a protease, a cellulase or an amylase.

27. A method according to claim 25, wherein the biopolymer degrading enzyme is incubated with the sample prior to step b) and/or after step c).

28. A method according to claim 1, wherein said incubation is performed at 30° C. to 60° C.

29. A method according to claim 28, wherein said incubation is performed at 35° C. to 50° C.

30. A method according to claim 1, wherein the buffer has a pH value greater than 7 and lower than 9.

31. A method according to claim 1, wherein said lysis solution comprises 0.2-2% of at least one detergent.

* * * * *

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer LIP1

<400> SEQUENCE: 1
gatacagaaa catcggttgg c                                              21

<210> SEQ ID NO 2
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer LIP2

<400> SEQUENCE: 2
gtgtaatctt gatgccatca g                                              21

<210> SEQ ID NO 3
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: TagMan Probe LIP-probe3

<400> SEQUENCE: 3
caggattaaa agttgaccgc a                                              21

<210> SEQ ID NO 4
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: TagMan probe Pluclm-4
```

```
<400> SEQUENCE: 4
ttcgaaatgt ccgttcggtt ggc                                             23

<210> SEQ ID NO 5
<211> LENGTH: 100
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: internal amplification control

<400> SEQUENCE: 5
gatacagaaa catcggttgg cgtattcgaa atgtccgttc ggttggcgct atgaagagat     60
acgcggtgga acctggaacc tgatggcatc aagattacac                          100
```